US012589172B2

(12) United States Patent
Kertser

(10) Patent No.: US 12,589,172 B2
(45) Date of Patent: Mar. 31, 2026

(54) ULTRAVIOLET DISINFECTION WITH AUGMENTED REALITY MONITORING

(71) Applicant: Atlantium Technologies Ltd, Beit-Shemesh (IL)

(72) Inventor: Michael Kertser, Bney Aish (IL)

(73) Assignee: Atlantium Technologies Ltd, Beit-Shemesh (IL)

( * ) Notice: Subject to any disclaimer, the term of this patent is extended or adjusted under 35 U.S.C. 154(b) by 403 days.

(21) Appl. No.: 18/254,856

(22) PCT Filed: Nov. 4, 2021

(86) PCT No.: PCT/IL2021/051308
§ 371 (c)(1),
(2) Date: May 28, 2023

(87) PCT Pub. No.: WO2022/130366
PCT Pub. Date: Jun. 23, 2022

(65) Prior Publication Data
US 2024/0050606 A1     Feb. 15, 2024

Related U.S. Application Data

(60) Provisional application No. 63/125,991, filed on Dec. 16, 2020.

(51) Int. Cl.
*A61L 2/10* (2026.01)
*G06T 7/00* (2017.01)
(Continued)

(52) U.S. Cl.
CPC .............. *A61L 2/10* (2013.01); *G06T 7/0002* (2013.01); *G06T 7/50* (2017.01); *G06T 7/73* (2017.01); *G06T 11/10* (2026.01); *A61L 2202/11* (2013.01); *A61L 2202/14* (2013.01)

(58) Field of Classification Search
CPC .... A61L 2/10; G06T 7/50; G06T 7/73; G06T 7/0002; G06T 11/001
See application file for complete search history.

(56) References Cited

U.S. PATENT DOCUMENTS

| | | |
|---|---|---|
| 2010/0104471 A1 | 4/2010 | Harmon et al. |
| 2018/0126021 A1 | 5/2018 | Valentine et al. |

(Continued)

FOREIGN PATENT DOCUMENTS

| | | |
|---|---|---|
| WO | WO 2017/020028 | 2/2017 |
| WO | WO 2019/241453 | 12/2019 |

(Continued)

OTHER PUBLICATIONS

Hui-Shyong Yeo, Juyoung Lee, Andrea Bianchi, David Harris-Birtill, and Aaron Quigley. 2017. SpeCam: Sensing Surface Color and Material with the Frontfacing Camera of a Mobile Device. In Proceedings of the 19th International Conference on HumanComputer Interaction with Mobile Devices and Services (MobileHCI '17), 25:1-25:9. Sep. 7, 2017 (Sep. 7, 2017).

(Continued)

*Primary Examiner* — Sean E Conley
(74) *Attorney, Agent, or Firm* — PEARL COHEN ZEDEK LATZER BARATZ LLP

(57) ABSTRACT

Augmented reality (AR) ultraviolet (UV) disinfection systems and methods are provided. AR UV disinfection systems comprise UV source(s) configured to irradiate a target with UV radiation, imaging unit(s) configured to image the target and derive depth information concerning the imaged target, AR processing unit(s) configured to estimate a UV radiation intensity delivered to multiple locations on the target by tempo-spatially integrating an intensity of the irradiated UV with respect to temporal and geometrical relations between the UV source and the locations on the target, as provided by the derived depth information, and to estimate a level of (Continued)

disinfection of the multiple locations on the target with respect to the estimated UV radiation intensity delivered thereto, and display(s) configured to visually present the estimated level of disinfection of the multiple locations upon a displayed image of the target.

11 Claims, 8 Drawing Sheets

(51) Int. Cl.

| | |
|---|---|
| *G06T 7/50* | (2017.01) |
| *G06T 7/73* | (2017.01) |
| *G06T 11/10* | (2026.01) |

(56) References Cited

U.S. PATENT DOCUMENTS

| | | |
|---|---|---|
| 2019/0117809 A1 | 4/2019 | Katz et al. |
| 2020/0179543 A1 | 6/2020 | Deshays et al. |
| 2020/0316238 A1 | 10/2020 | Zhang et al. |

FOREIGN PATENT DOCUMENTS

| | | |
|---|---|---|
| WO | WO 2021/195003 | 9/2021 |
| WO | WO 2021/202895 | 10/2021 |

OTHER PUBLICATIONS

International Search Report dated Jan. 27, 2022 for PCT Application No. PCT/IL2021/051308.

Gabriel Chevrefils et al; UV dose required to achieve incremental log inactivation of bacteria, protozoa and viruses; IUVA News/vol. 8 No. 1; Mar. 2006.

Do-Kyun Kim et al.; UVC LED Irradiation Effectively Inactivates Aerosolized Viruses, Bacteria, and Fungi in a Chamber-Type Air Disinfection System; Sep. 2018 vol. 84 Issue 17 e00944-18 Applied and Environmental Microbiology.

Martin Heßling et al; Ultraviolet irradiation doses for coronavirus inactivation—review and analysis of coronavirus photoinactivation studies; GMS Hygiene and Infection Control. 2020; 15: Doc08.; Published online May 14, 2020.

Samuel K. Moore; Flight of the GermFalcon—How a potential coronavirus-killing airplane sterilizer was born;Tech Talk-Aerospace-Aviation; Mar. 9, 2020, IEEE Spectrum.

Stop

Clean

_145_

_140_

_141_

_142_

_142_

_142_

Scan

Clean

_145_

_140_

141    142

142

Scan          Clean

145

_140_

141

142

Scan          Clean 142          145

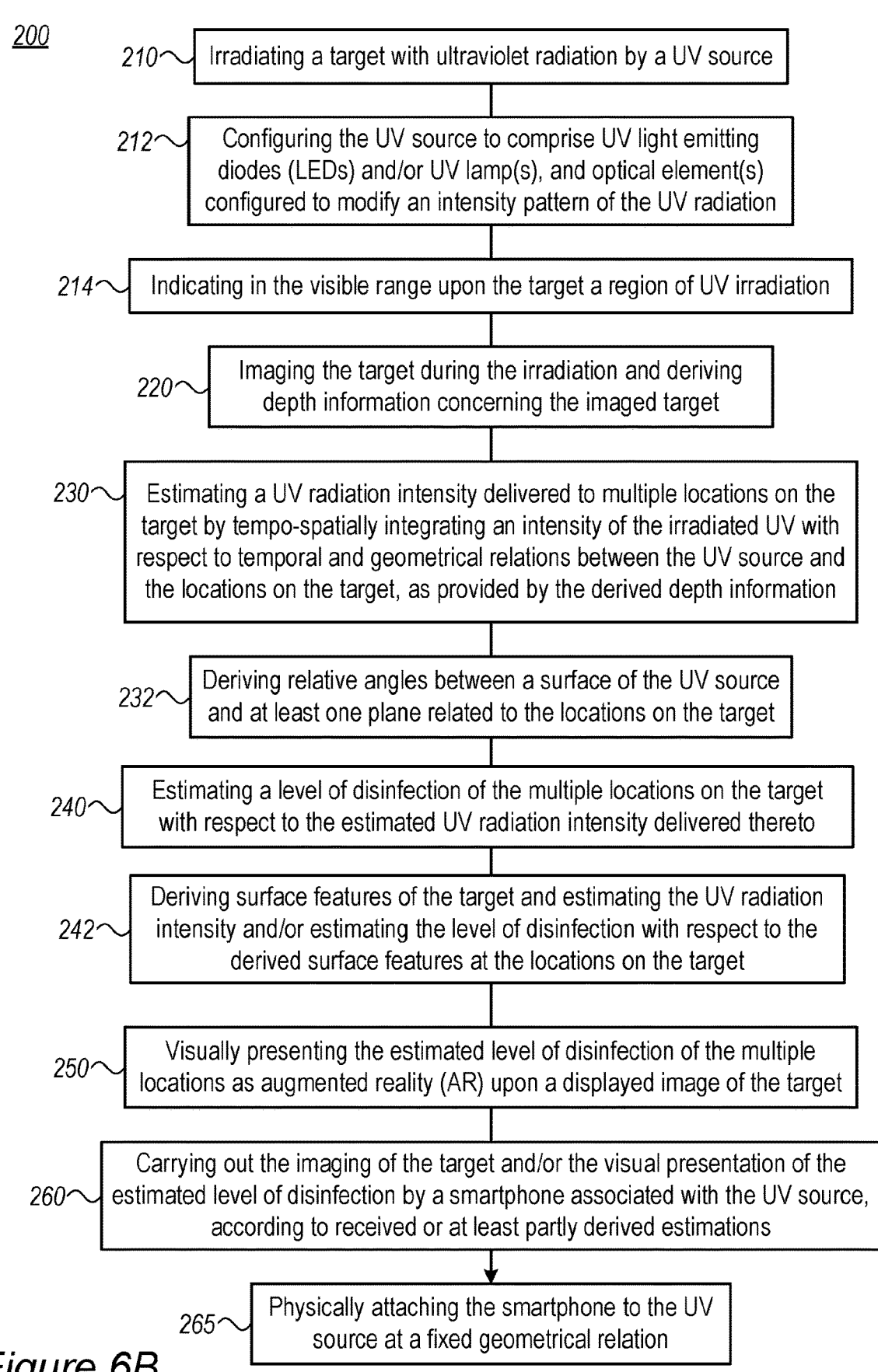

*200*

210 — Irradiating a target with ultraviolet radiation by a UV source

212 — Configuring the UV source to comprise UV light emitting diodes (LEDs) and/or UV lamp(s), and optical element(s) configured to modify an intensity pattern of the UV radiation 214 — Indicating in the visible range upon the target a region of UV irradiation 220 — Imaging the target during the irradiation and deriving depth information concerning the imaged target 230 — Estimating a UV radiation intensity delivered to multiple locations on the target by tempo-spatially integrating an intensity of the irradiated UV with respect to temporal and geometrical relations between the UV source and the locations on the target, as provided by the derived depth information 232 — Deriving relative angles between a surface of the UV source and at least one plane related to the locations on the target 240 — Estimating a level of disinfection of the multiple locations on the target with respect to the estimated UV radiation intensity delivered thereto 242 — Deriving surface features of the target and estimating the UV radiation intensity and/or estimating the level of disinfection with respect to the derived surface features at the locations on the target 250 — Visually presenting the estimated level of disinfection of the multiple locations as augmented reality (AR) upon a displayed image of the target 260 — Carrying out the imaging of the target and/or the visual presentation of the estimated level of disinfection by a smartphone associated with the UV source, according to received or at least partly derived estimations 265 — Physically attaching the smartphone to the UV source at a fixed geometrical relation

*Figure 6B*

ULTRAVIOLET DISINFECTION WITH AUGMENTED REALITY MONITORING

CROSS-REFERENCE TO RELATED APPLICATIONS

This application is a National Phase Application of PCT International Application No. PCT/IL2021/051308, International Filing Date Nov. 4, 2021, claiming the benefit of U.S. Patent Application No. 63/125,991, filed Dec. 16, 2020, which is hereby incorporated by reference.

BACKGROUND OF THE INVENTION

1. Technical Field

The present invention relates to the field of ultraviolet (UV) disinfection, and more particularly, to monitoring systems and methods for UV disinfection.

2. Discussion of Related Art

The need to disinfect targets from pathogens increases, e.g., disinfection of seats and surfaces in public transportation and disinfection of a wide range of objects to eliminate viral pathogens—are highly required.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides an augmented reality (AR) ultraviolet (UV) disinfection system comprising: a UV source configured to irradiate a target with UV radiation, an imaging unit configured to image the target and derive depth information concerning the imaged target, an AR processing unit configured to estimate a UV radiation intensity delivered to multiple locations on the target by tempo-spatially integrating an intensity of the irradiated UV with respect to temporal and geometrical relations between the UV source and the locations on the target, as provided by the derived depth information, and to estimate a level of disinfection of the multiple locations on the target with respect to the estimated UV radiation intensity delivered thereto, and a display configured to visually present the estimated level of disinfection of the multiple locations upon a displayed image of the target.

One aspect of the present invention provides a method comprising: irradiating a target with ultraviolet (UV) radiation by a UV source, imaging the target during the irradiation and deriving depth information concerning the imaged target, estimating a UV radiation intensity delivered to multiple locations on the target by tempo-spatially integrating an intensity of the irradiated UV with respect to temporal and geometrical relations between the UV source and the locations on the target, as provided by the derived depth information, estimating a level of disinfection of the multiple locations on the target with respect to the estimated UV radiation intensity delivered thereto, and visually presenting the estimated level of disinfection of the multiple locations as augmented reality (AR) upon a displayed image of the target.

One aspect of the present invention provides a computer program product comprising a non-transitory computer readable storage medium having computer readable program embodied therewith, the computer readable program comprising: computer readable program configured to image a target during ultraviolet (UV) irradiation thereof and deriving depth information concerning the imaged target, computer readable program configured to estimate a UV radiation intensity delivered to multiple locations on the target by tempo-spatially integrating an intensity of the irradiated UV with respect to temporal and geometrical relations between the UV source and the locations on the target, as provided by the derived depth information, and computer readable program configured to estimate a level of disinfection of the multiple locations on the target with respect to the estimated UV radiation intensity delivered thereto, to yield a visual presentation of the estimated level of disinfection of the multiple locations as augmented reality (AR) upon a displayed image of the target.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1 illustrates prior art UV disinfection, according to the prior art.

FIG. 6B is a high-level flowchart illustrating method, according to some embodiments of the invention.

Figure 2:
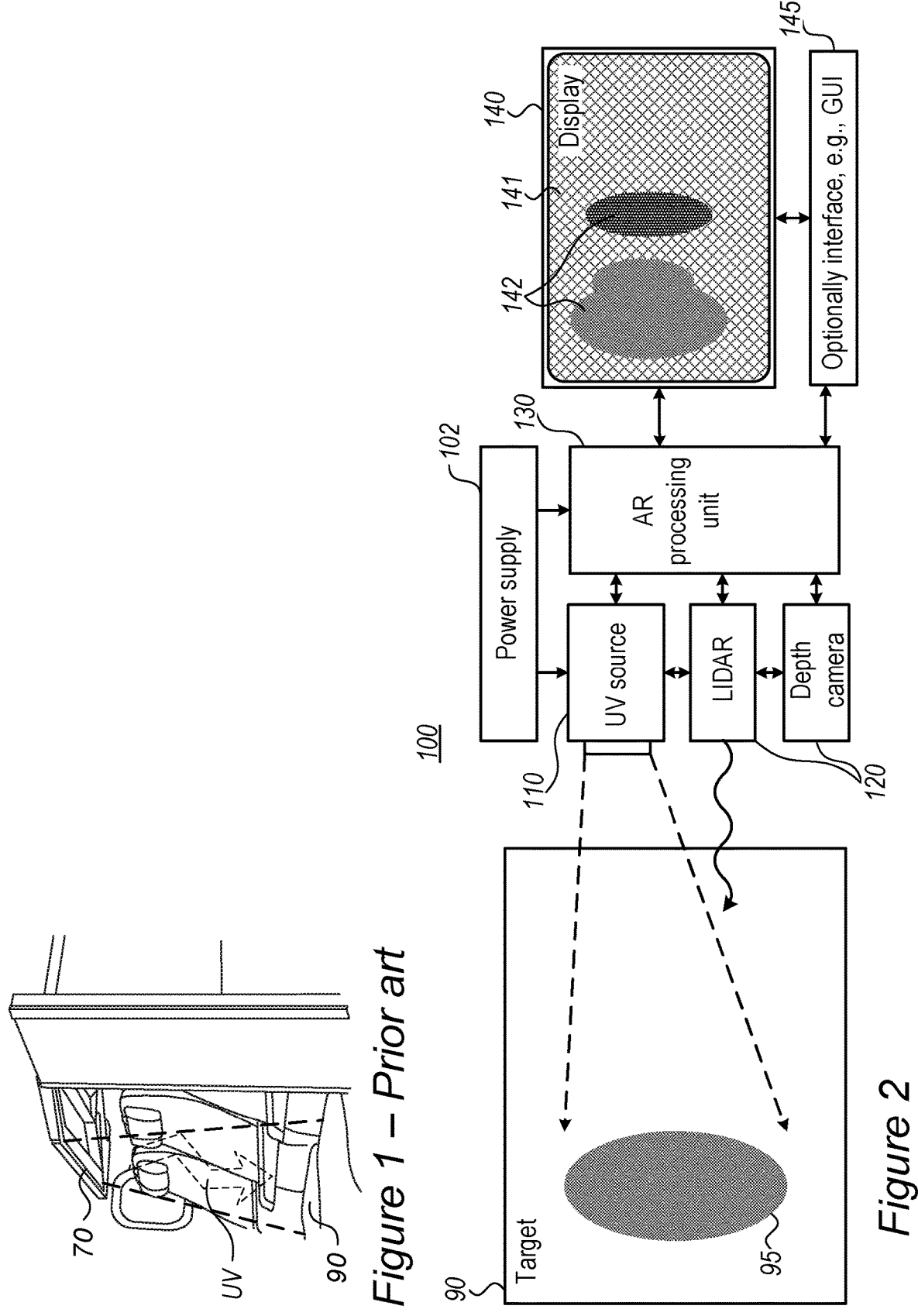
FIG. 2 is a high-level schematic block diagram of augmented reality (AR) ultraviolet (UV) disinfection system, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention.

However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing", "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention provide efficient and economical methods and mechanisms for disinfecting targets and thereby provide improvements to the technological field of hygiene and sanitation, particularly to protection against pathogens. Augmented reality (AR) ultraviolet (UV) disinfection systems and methods are provided. AR UV disinfection systems comprise UV source(s) configured to irradiate a target with UV radiation, imaging unit(s) configured to image the target and derive depth information concerning the imaged target, AR processing unit(s) configured to estimate a UV radiation intensity delivered to multiple locations on the target by tempo-spatially integrating an intensity of the irradiated UV with respect to temporal and geometrical relations between the UV source and the locations on the target, as provided by the derived depth information, and to estimate a level of disinfection of the multiple locations on the target with respect to the estimated UV radiation intensity delivered thereto, and display(s) configured to visually present the estimated level of disinfection of the multiple locations upon a displayed image of the target. AR UV disinfection systems may be associated with mobile communication devices such as smartphones, utilizing the display, imaging units and processing power of the devices to enhance the performance of AR UV disinfection systems.

FIG. 1 illustrates prior art UV disinfection, according to the prior art. Stationary or portable UV disinfection systems

70 are implemented to disinfect targets 90 by UV, such as various surface and objects, e.g., aircraft seats in the illustrated example. However, UV disinfection in the prior art is not controlled and may yield partial disinfection (e.g., by delivering a low UV dose, due to shading or masking, etc.) or damage to the treated surfaces or objects.

Figures 3A, 3B:
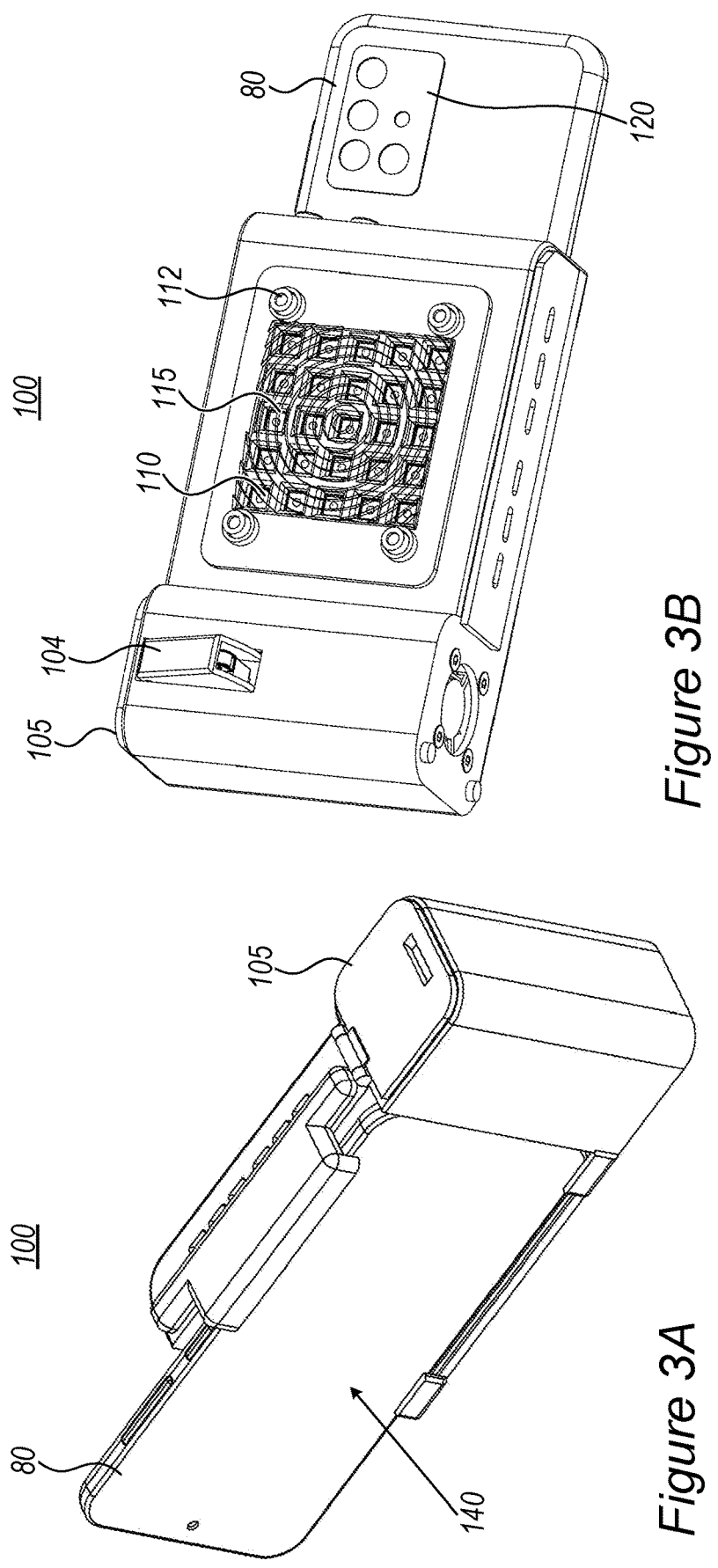
FIGS. 3A-3D are schematic high-level illustrations of AR UV disinfection systems, according to some embodiments of the invention.
Figures 3C, 3D:
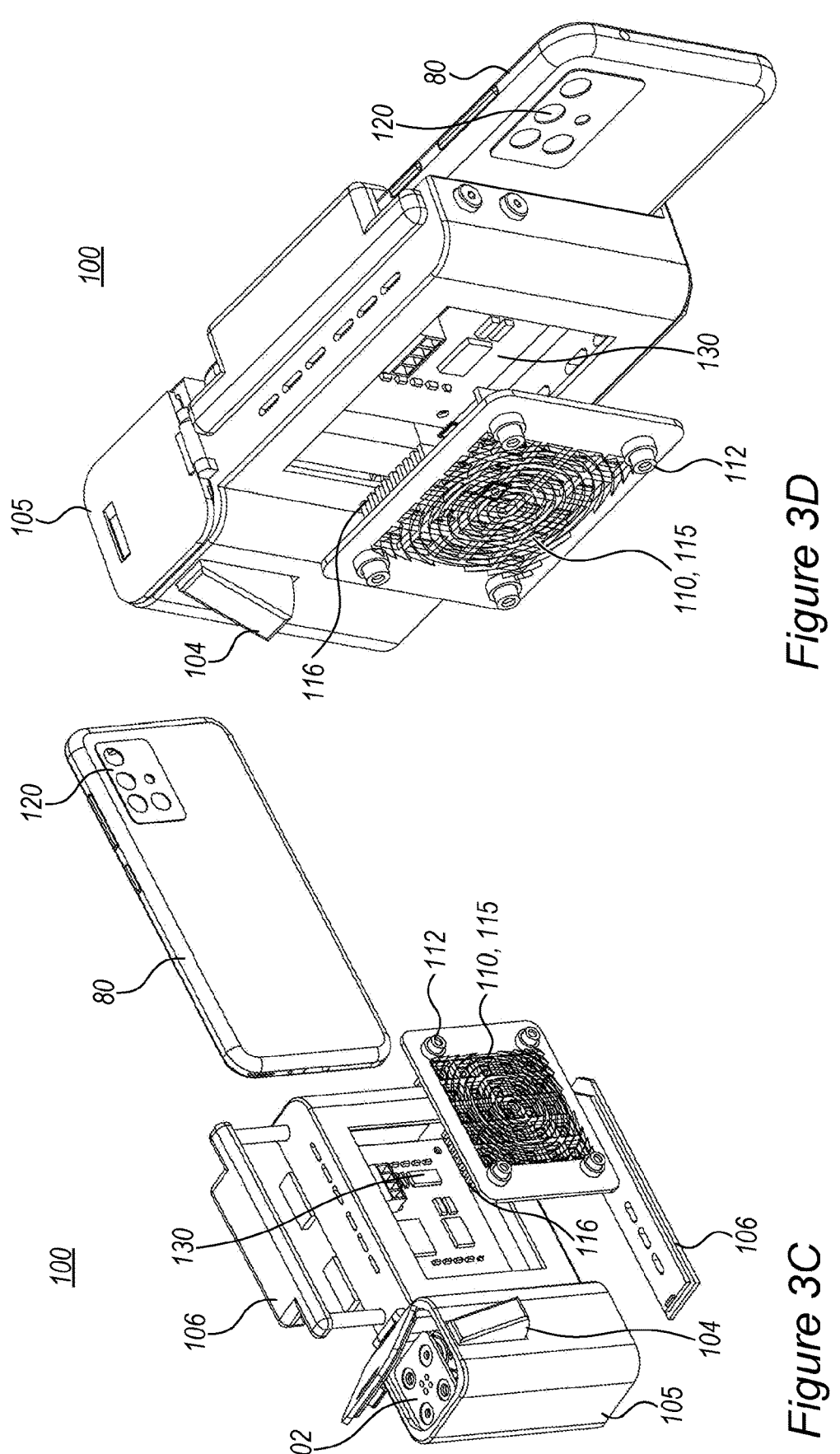

FIG. 2 is a high-level schematic block diagram of augmented reality (AR) ultraviolet (UV) disinfection system 100, according to some embodiments of the invention. FIGS. 3A-3D are schematic high-level illustrations of AR UV disinfection system 100, according to some embodiments of the invention. FIGS. 3A and 3B are perspective views from two sides of AR UV disinfection system 100 and FIGS. 3C and 3D are exploded views from two sides of AR UV disinfection system 100, according to some embodiments of the invention.

AR UV disinfection system 100 comprises UV source 110 configured to irradiate a target 90 with UV radiation, an imaging unit 120 configured to image target 90 and derive depth information concerning the imaged target, an AR processing unit 130 configured to estimate a UV radiation intensity delivered to multiple locations 95 on target 90 by tempo-spatially integrating an intensity of the irradiated UV with respect to temporal and geometrical relations between UV source 110 and locations 95 on target 90, as provided by the derived depth information, and to estimate a level of disinfection of the multiple locations on the target with respect to the estimated UV radiation intensity delivered thereto, and a display 140 configured to visually present the estimated level of disinfection of the multiple locations (e.g., as color codes 142 over an AR grid 141, illustrated schematically) upon a displayed image of the target. For example, categories of disinfection levels may be indicated by color, as shown schematically in FIG. 2 and in the example in FIGS. 5A-5D. Optionally, a user interface 145 may be used to modify operation and adjust parameters AR UV disinfection system 100. Optionally, parts of AR UV disinfection system 100 (e.g., processing, imaging and/or display modules) may be implemented in associated mobile devices such as smartphones, as disclosed below.

Advantageously, disclosed AR UV disinfection system 100 provide continuous monitoring of the UV dose delivered to the surfaces or objects that are disinfected and may be configured to adjust the monitored UV dose with respect to target geometry, materials as well as with respect to movements of the UV source in case of portable devices. AR UV disinfection system 100 may be configured to calculated required UV doses with respect to the target and relate the applied UV dose to the calculated required dose, e.g., for different surfaces of the target. AR UV disinfection system 100 may be configured to receive from the user a required level if UV disinfection, or a required UV dose, and indicate reaching the required threshold on display 140. Alternatively or complementary, the accumulating UV dose may be presented on display 140, and the user may decide concerning further application of UV disinfection, e.g., with respect to completeness and throughput considerations. AR may be used to indicate any of the applied UV dose, required UV dose and/or the difference between required and applied UV dose, e.g., in percent, color code, audio signals, or any other mode. The required UV dose may be adjusted with respect to surface characteristics such as optical quality, absorption characteristics, diffusivity, etc.—to enhance the accuracy of calculating the required UV dose.

AR UV disinfection system 100 may further comprise safety features such as detection of obstructing body parts or other objects and indication thereof. AR UV disinfection system 100 may be configured to halt UV radiation in case an obstructing body part is detected.

UV source 110 may be fed, e.g., by a power source 102, possibly an accumulator-based power supply. UV source 110 may be cooled by a cooling unit 116 (see, e.g., FIGS. 3C and 3D), that may also be supplied by power source 102. Non-limiting examples for UV source 110 include an array of 64 (8=8) 265 nm 3 mW LEDs, sufficient to disinfect a 115 cm² surface at 20 cm distance by a 2.5 sec application (for typically viral UV 10-times reduction of ca. 4 mJ/cm²). Such application required 5-10 W which may be dissipated by passive cooling (e.g., aluminum heat-sink), higher power application may require active cooling. Clearly, any UV disinfection threshold may be selected (for various pathogens and for various levels of disinfection, e.g., 90%, 99%, 99.9% etc.), and AR UV disinfection system 100 may be configured to carry out the UV irradiation estimations respectively.

In certain embodiments, at least imaging unit 120 and display 140 may be part of a smartphone 80 that is configured to receive and display the estimated level of disinfection from AR processing unit 130. In certain embodiments at least a part of AR processing unit 130 may also be implemented by a processing unit of smartphone 80, supporting the required calculations, e.g., performing at least a part of the depth information, as well as performing related geometrical calculations, surface characterization, radiation intensity integration and AR display parameters, as disclosed herein. AR UV disinfection system 100 may further comprise a user interface 145, e.g., a GUI (graphical user interface) implemented with display 140 of the smartphone.

As illustrated, e.g., in FIGS. 3A-3D, AR UV disinfection system 100 may further comprise a housing 105 configured to hold UV source 110, optionally power source 102 (illustrated in a non-limiting manner as batteries in housing 105) for UV source 110 (activated, e.g., by actuator 104), and optionally at least part of AR processing unit 130—at a fixed geometrical relation with respect to smartphone 80. Printed circuit card 130 in FIGS. 3A-3D may be considered as fully or partly implementing AR processing unit 130, optionally with additional processing modules implemented in the processing units of smartphone.

UV source 110 may comprise an array of UV light emitting diodes (LEDs) and/or at least one UV Hg lamp. For example, UV source 110 may comprise a 5 by 5 LED array arranged as a square or rectangle. Additionally or in place of some of the LEDs, one or more UV lamp may be integrated into UV source 110, e.g., to modify the illumination pattern, intensity profile and/or wavelength ranges. In another example, UV source 110 may comprise four UV lamps arranged as a square or rectangle. Additionally or in place of some of the UV lamps, one or more UV LEDs may be integrated into UV source 110, e.g., to modify the illumination pattern, intensity profile and/or wavelength ranges.

In certain embodiments, UV source 110 may comprise an external UV source (for example a powerful UV projector, see, e.g., stationary or portable UV disinfection systems 70 illustrated in FIG. 1), and imaging unit 120 may be configured to track optical trace ray marks from the external UV source on the irradiated surface of target 90. AR processing unit 130 may accordingly be configured to estimate the UV radiation intensity delivered to multiple locations on the target by tempo-spatially integrating an intensity of the irradiated UV with respect to temporal and geometrical relations between the external UV source (e.g., UV projector) and the locations on the target, as provided by the derived depth information from imaging unit 120, and to estimate a level of disinfection of the multiple locations on the target with respect to the estimated UV radiation intensity delivered thereto.

UV source 110 may comprise at least one optical element 115 configured to modify an intensity pattern of the UV radiation from UV source. For example, optical element(s) 115 may comprise one or more lenses, e.g., Fresnel lens illustrated as a non-limiting example in FIGS. 3B-3D). Different optical elements 115 may be used for the center of the illumination area of UV source 110 with respect to edges of the illumination area of UV source 110 and/or for different types of parts of UV source 110, e.g., for UV LEDs or for UV lamps. AR processing unit 130 may be further configured to estimate the UV radiation intensity with respect to the modified UV intensity pattern—as provided by optical element(s) 115 in association with the UV LEDs and/or UV lamps.

Figure 4B:
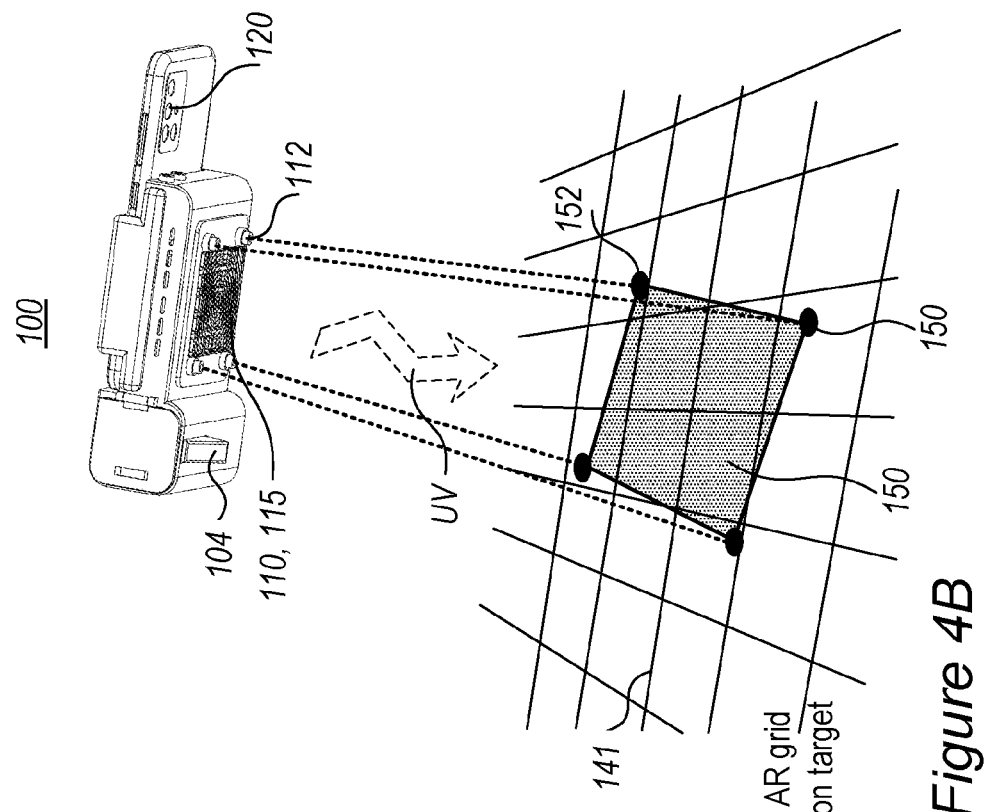
FIGS. 4A and 4B are schematic high-level illustrations of geometrical considerations implemented by AR UV disinfection systems, according to some embodiments of the invention.

In certain embodiments, AR UV disinfection system 100 may further comprise at least one optical element 112 in the visible range, configured to indicate upon target 80 a region of UV irradiation—to simplify operation of AR UV disinfection system 100. For example, as illustrated in FIG. 4B, four dots 152 from optical element(s) 112 at the corners of UV source 110 may be used to indicate the approximate edges of the region of target 90 that is illuminated by UV source 110. In other examples, optical element(s) 112 may be configured to illuminate an approximate border (e.g., as points, curves, lines, etc.) of the illuminated region, or one or more approximated line of equal illumination intensity—to allow the user judicious enhancement of the level of disinfection of target 90.

Figure 4A:
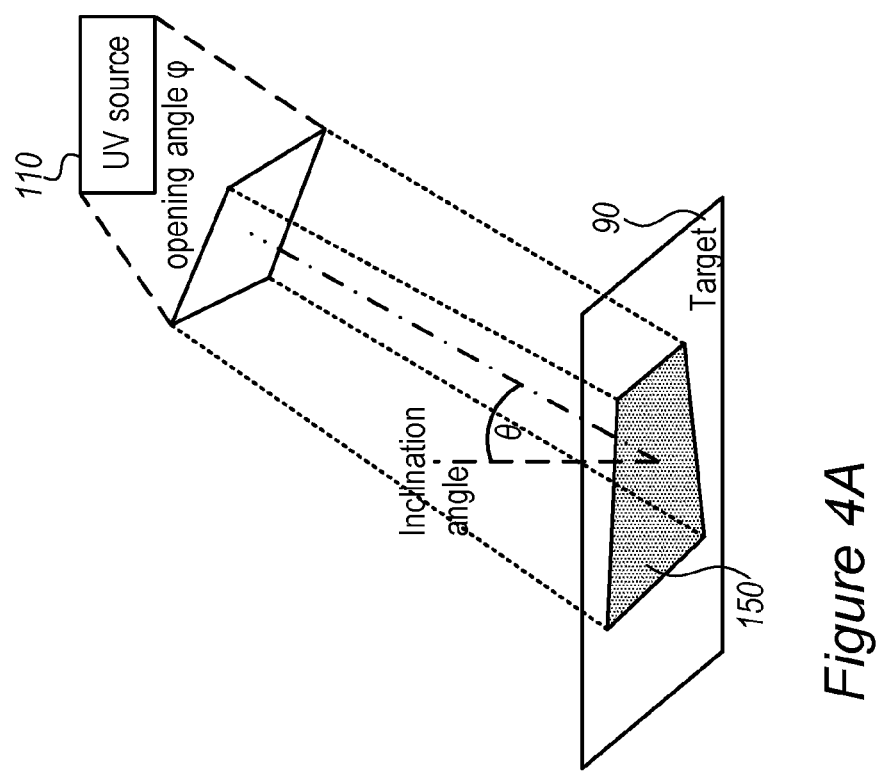

FIGS. 4A and 4B are schematic high-level illustrations of geometrical considerations implemented by AR UV disinfection system 100, according to some embodiments of the invention. Imaging unit 120 may be configured to measure the distances between UV source 110 and multiple locations on target 90, e.g., using LIDAR (laser imaging, detection, and ranging) data and/or depth camera data. Imaging unit 120 may be further configured to derive relative angles between a surface of UV source 110 and at least one plane 150 related to the locations on target 90. For example, in the simplified illustration of FIG. 4A, 6 denotes the relative angle between a flat imaged region 150 on target 90 and the imaging plane of imaging unit 120 which parallel to UV source 110 in the non-limiting example illustrated schematically in FIG. 4B. In typical applications, target 90 may comprise multiple surfaces or uneven regions, and imaging unit 120 may be configured to derive the relative angles between some or all of the surfaces and UV source 110, with AR processing unit 130 calculating the respective projections of UV source 110 on the respective surfaces to derive the momentary intensity of UV radiation from the calculated projections. AR processing unit 130 may be further configured to integrate, for each target location, the momentary intensity of UV radiation over time, with respect to changes in the relative position and relative orientation of UV source 110 with respect to the locations on target 90.

The following is a non-limiting simplified example for using the geometrical considerations to calculate the UV dose. It is noted that empirical calibration and adjustments may be applied to adjust the estimations of the UV radiation intensity doses. For example, with UV source 110 as a LED matrix with a fixed opening angle $\varphi$ for every LED unit and a specific near-square radiant pattern, the effective irradiance may be expressed as in Equations 1, as a correction factor $CF(\varphi)$ multiplied by the projection of the radiant intensity $I_0$ $\cos \theta$ over the surface area (taking into account the angle $\theta$ 7                                                                    8 between UV source 110 and surface 150 as illustrated schematically in FIG. 4A) at distance r derived from the depth measurements. The UV dose $D_{UV}$ may be derived by integration of $I_r$ over time, e.g., by simple multiplication in case the UV irradiation remains constant in position.

$$I_r = \frac{CF(\varphi) * I_0\cos\theta}{r^2} \qquad \text{Equations 1}$$

$$D_{UV}\left[\frac{mJ}{cm^2}\right] = \frac{CF(\varphi) * I_0[mW]\cos\theta}{r^2[cm^2]} * \Delta t[sec]$$

In addition to integrating of the momentary UV dose for each target location with respect to the geometrical relation and duration of irradiance, imaging unit 120 and/or AR processing unit 130 may be further configured to derive and/or take into further consideration surface features of the target (e.g., quantify specular, diffuse reflective and/or absorptive spectral properties, as well as material composition and UV absorption parameters)—and estimate the UV radiation intensity and/or the level of disinfection with respect to the derived surface features at the locations on the target.

Figure 5A:
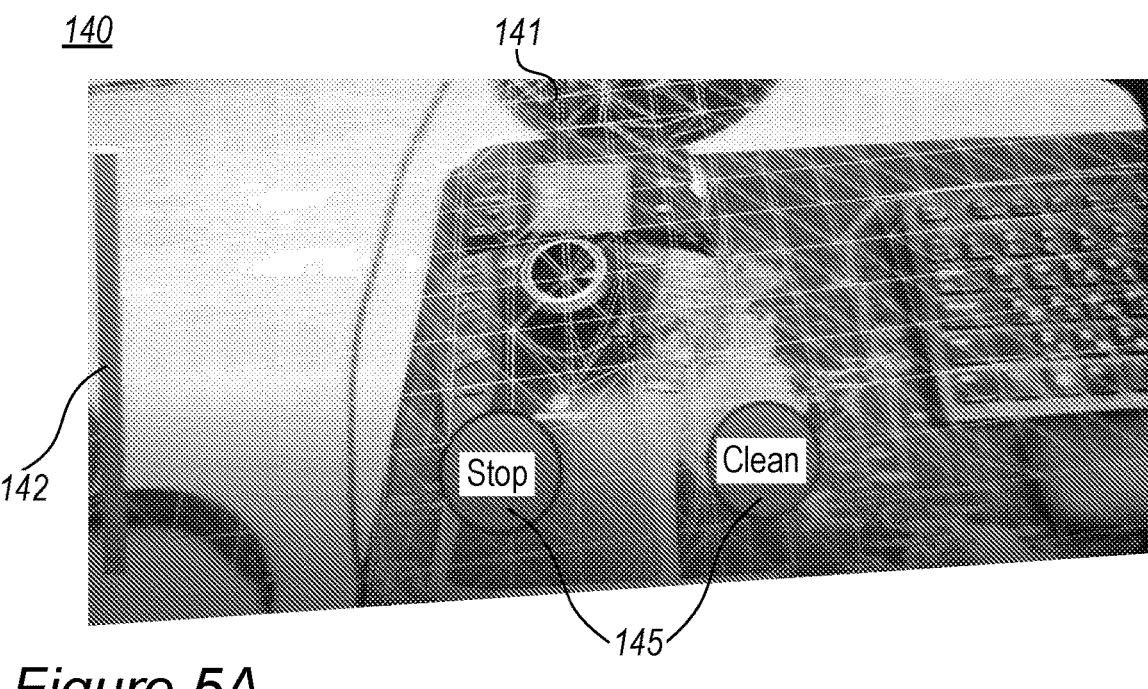
FIGS. 5A-5D are schematic high-level examples of AR display and interface with color-coded levels of UV disinfection derived by AR UV disinfection system, according to some embodiments of the invention.
Figure 5B:
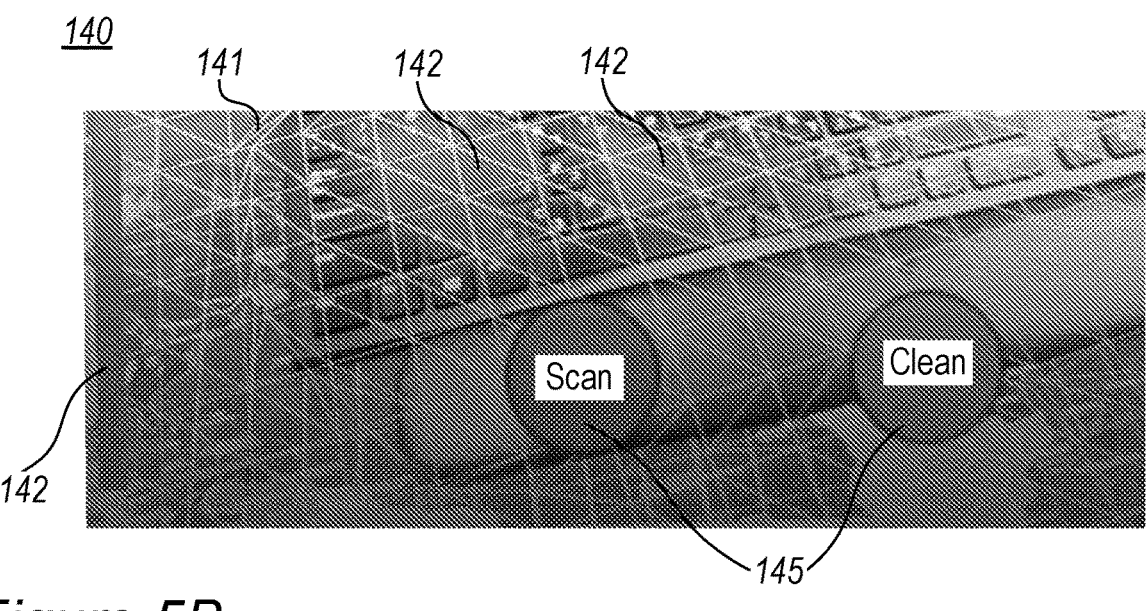
Figure 5C:
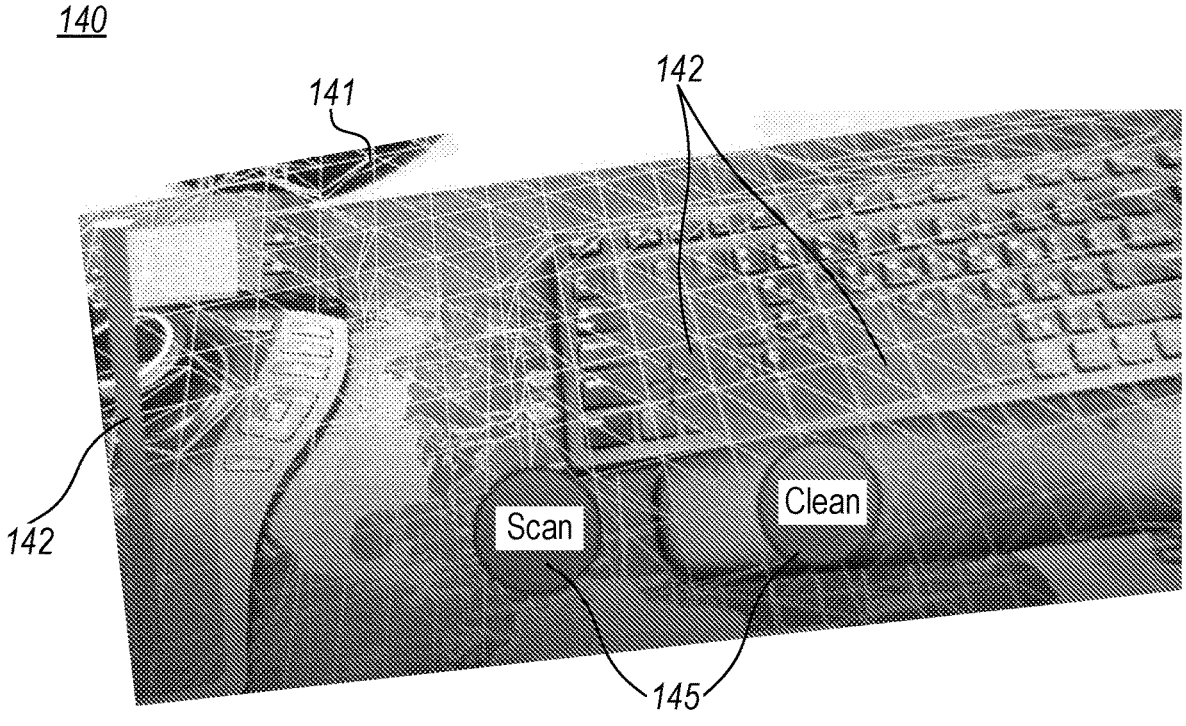
Figure 5D:
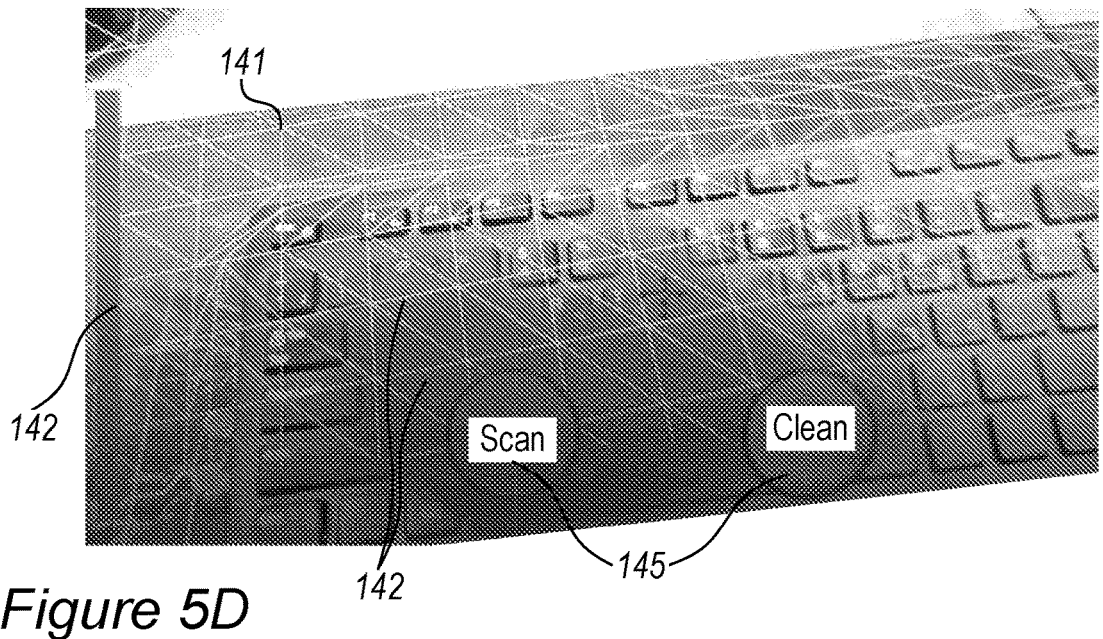

FIGS. 5A-5D are schematic high-level examples of AR display 140 and interface 145 with color-coded levels of UV disinfection derived by AR UV disinfection system 100, according to some embodiments of the invention. AR display 140 may be overlaid upon a camera image (e.g., from imaging unit 120 and/or a smartphone camera), illustrated schematically in a non-limiting manner as an AR triangular grid 141 indicating the surfaces into which target 90 may be modelled for the AR display, and levels of UV disinfection (e.g., corresponding to the integrated received UV radiation intensity per surface) may be overlaid in color code 142. For example, consecutive FIGS. 5B-5D illustrate local and overall increases in the level of UV disinfection, from green to red colors. Interface 145 may be implemented as enabling display refreshes, or in association with UV activation (e.g., in addition or in place of actuator 104. The user may move, rotate and adjust the position and/or orientation of UV source 110 (e.g., by moving AR UV disinfection system 100 with smartphone 80 attached in housing 105, e.g., by elements 106, see FIG. 3C) to enhance UV radiation received by certain surfaces of target 90 to verify complete disinfection, as indicated on display 140. In certain embodiments, the user may use interface 145 to modify UV radiation intensity in certain regions, e.g., using a touch interface.

Figure 6A:
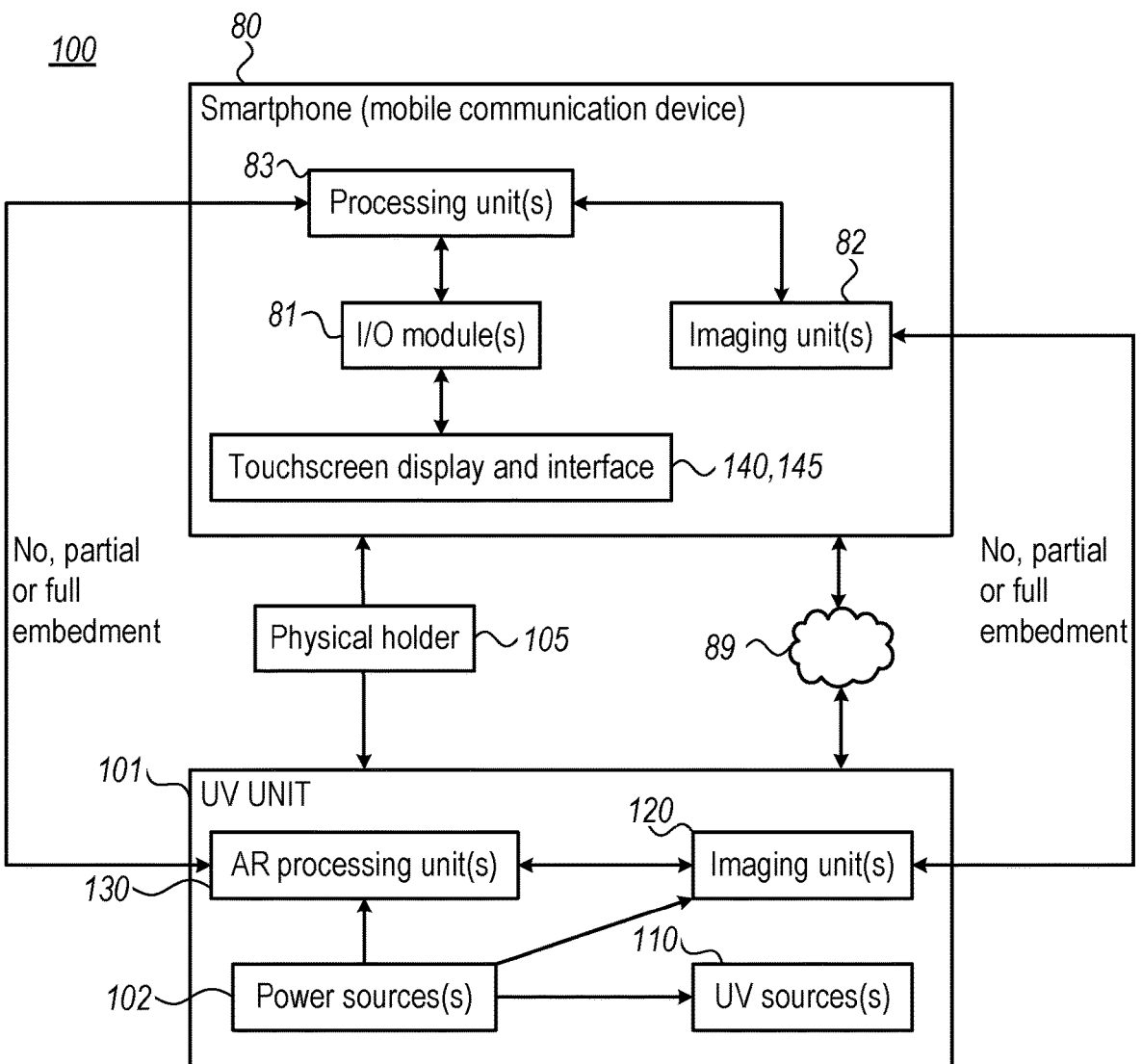
FIG. 6A is a high-level block diagram illustrating AR UV disinfection systems, according to some embodiments of the invention.

FIG. 6A is a high-level block diagram illustrating AR UV disinfection system 100, according to some embodiments of the invention. FIG. 6B is a high-level flowchart illustrating a method 200, according to some embodiments of the invention. The method stages may be carried out with respect to AR UV disinfection system 100 described herein, which may optionally be configured to implement method 200. Elements from FIGS. 2-6B may be combined in any operable combination, and the illustration of certain elements in certain figures and not in others merely serves an explanatory purpose and is non-limiting.

As illustrated schematically in FIG. 6A, a UV unit 101 may comprise UV source(s) 120, imaging unit(s) 120 and/or AR processing unit(s) 130, and power source(s) 102 feeding UV source(s) 120. In various configurations, mobile communication device(s) 80 such as smartphone(s) 80, laptop computers, etc. may be used in association with UV unit 101, with no, partial or full embedment of imaging unit(s) 120 and/or AR processing unit(s) 130 in imaging unit(s) 82 and/or processing unit(s) 83, respectively, of mobile communication device(s) 80 such as smartphone(s) 80. I/O module(s) 81 of mobile communication device(s) 80 such as smartphone(s) 80 may be used to display the AR data such as the estimated level of disinfection of locations on the target on display 140 and optionally receive input from the user via interface 145 such as GUI of mobile communication device 80 such as smartphone 80. UV unit 101 may be attached physically to mobile communication device 80 such as smartphone 80, e.g., by holder 105 (e.g., by elements 106, see FIG. 3C) and/or be connected thereto over wire or wirelessly, over communication link(s) 89.

Processing unit(s) 83 may include at least one processor (associated with at least one memory unit(s)) configured to execute computer programs, applications, methods, processes, or other software to perform embodiments described in the present disclosure. For example, the processing unit(s) may include one or more integrated circuits, microchips, microcontrollers, microprocessors, all or part of a central processing unit (CPU), graphics processing unit (GPU), digital signal processor (DSP), field programmable gate array (FPGA), or other circuits suitable for executing instructions or performing logic operations. The processing unit(s) may include at least one processor configured to perform functions of the disclosed methods such as various available microprocessors. The processing unit(s) may include a single core or multiple core processors executing parallel processes simultaneously. In one example, the processing unit(s) may be a single core processor configured with virtual processing technologies. The processing unit(s) may implement virtual machine technologies or other technologies to provide the ability to execute, control, run, manipulate, store, etc., multiple software processes, applications, programs, etc. In another example, the processing unit(s) may include a multiple-core processor arrangement (e.g., dual, quad core, etc.) configured to provide parallel processing functionalities to allow a device associated with the processing unit(s) to execute multiple processes simultaneously. It is appreciated that other types of processor arrangements could be implemented to provide the capabilities disclosed herein.

Method 200 may be at least partially implemented by at least one computer processor illustrated in FIG. 6B. Certain embodiments comprise computer program products comprising a computer readable storage medium having computer readable program embodied therewith and configured to carry out the relevant stages of method 200. Method 200 may comprise the following stages, irrespective of their order.

Method 200 comprises irradiating a target with ultraviolet (UV) radiation by a UV source (stage 210), imaging the target during the irradiation and deriving depth information concerning the imaged target (stage 220), estimating a UV radiation intensity delivered to multiple locations on the target by tempo-spatially integrating an intensity of the irradiated UV with respect to temporal and geometrical relations between the UV source and the locations on the target, as provided by the derived depth information (stage 230), estimating a level of disinfection of the multiple locations on the target with respect to the estimated UV radiation intensity delivered thereto (stage 240), and visually presenting the estimated level of disinfection of the multiple locations as augmented reality (AR) upon a displayed image of the target (stage 250).

Method 200 may further comprise carrying out at least the imaging of the target and the visually presenting the estimated level of disinfection by a smartphone associated with the UV source, according to received or at least partly derived estimations (stage 260). For example, method 200 may further comprise physically attaching the smartphone to the UV source at a fixed geometrical relation (stage 265) and/or communicating with the smartphone via communication link(s).

Method 200 may further comprise configuring the UV source to comprise an array of UV light emitting diodes (LEDs) and/or at least one UV lamp and configuring at least one optical element to modify an intensity pattern of the UV radiation (stage 212).

Method 200 may further comprise indicating in the visible range upon the target a region of UV irradiation (stage 214), e.g., applying dots or lines to indicated the irradiated area.

Method 200 may further comprise deriving relative angles between a surface of the UV source and at least one plane related to the locations on the target (stage 232).

Method 200 may further comprise deriving surface features of the target and estimating the UV radiation intensity and/or estimating the level of disinfection with respect to the derived surface features at the locations on the target (stage 242).

Examples for computer program products comprise a non-transitory computer readable storage medium having computer readable program embodied therewith, the computer readable program comprising: computer readable program configured to image a target during ultraviolet (UV) irradiation thereof and deriving depth information concerning the imaged target, computer readable program configured to estimate a UV radiation intensity delivered to multiple locations on the target by tempo-spatially integrating an intensity of the irradiated UV with respect to temporal and geometrical relations between the UV source and the locations on the target, as provided by the derived depth information, computer readable program configured to estimate a level of disinfection of the multiple locations on the target with respect to the estimated UV radiation intensity delivered thereto, to yield a visual presentation of the estimated level of disinfection of the multiple locations as augmented reality (AR) upon a displayed image of the target.

In certain embodiments, the computer program product may further comprise computer readable program configured to derive relative angles between a surface of a UV source and at least one plane related to the locations on the target and/or computer readable program configured to derive surface features of the target and estimate the UV radiation intensity and/or estimate the level of disinfection with respect to the derived surface features at the locations on the target.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An augmented reality (AR) ultraviolet (UV) disinfection system comprising:
   a UV source configured to irradiate a target with UV radiation,
   an imaging unit configured to image the target and derive depth information concerning the imaged target,
   at least one optical element in the visible range, configured to indicate upon the target approximate edges of a region of the target that is illuminated by UV irradiation and/or one or more approximated line of equal illumination intensity within a region of the target that is illuminated by UV irradiation to allow the user enhancement of the level of disinfection of target,
   an AR processing unit configured to:
      estimate a UV radiation intensity delivered to multiple locations on the target by tempo-spatially integrating an intensity of the irradiated UV with respect to temporal and geometrical relations between the UV source and the locations on the target, within the indicated region, as provided by the derived depth information, and
      estimate a level of disinfection of the multiple locations on the target with respect to the estimated UV radiation intensity delivered thereto, and
   a display configured to visually present the estimated level of disinfection of the multiple locations upon a displayed image of the target.

2. The AR UV disinfection system of claim 1, wherein at least the imaging unit and the display are part of a smartphone, wherein the smartphone is configured to receive and display the estimated level of disinfection from the AR processing unit.

3. The AR UV disinfection system of claim 2, wherein at least a part of the AR processing unit is implemented by a processing unit of the smartphone.

4. The AR UV disinfection system of claim 2, further comprising a housing configured to hold the UV source, optionally a power source for the UV source, and optionally at least part of the AR processing unit—at a fixed geometrical relation with respect to the smartphone.

5. The AR UV disinfection system of claim 1, wherein the UV source comprises an array of UV light emitting diodes (LEDs) and/or at least one UV lamp.

6. The AR UV disinfection system of claim 5, wherein the UV source further comprises at least one another optical element configured to modify an intensity pattern of the UV radiation, and the AR processing unit is further configured to estimate the UV radiation intensity with respect to the modified UV intensity pattern.

7. The AR UV disinfection system of claim 1, wherein the imaging unit is further configured to derive relative angles between a surface of the UV source and at least one plane related to the locations on the target within the indicated region.

8. The AR UV disinfection system of claim 7, wherein the imaging unit is further configured to derive surface features of the target within the indicated region and the AR processing unit is further configured to estimate the UV radiation intensity and/or to estimate the level of disinfection with respect to the derived surface features at the locations on the target.

9. The AR UV disinfection system of claim 1, further configured to calculate required UV doses with respect to the target and relate the applied UV dose to the calculated required dose.

10. The AR UV disinfection system of claim 1, further configured to present an accumulating UV dose on the display, to allow a user to decide concerning further application of UV disinfection.

11. The AR UV disinfection system of claim 1, further configured to indicate at least one of: the applied UV dose, a required UV dose and/or a difference between a required and the applied UV dose.

* * * * *